United States Patent [19]

Holtkamp

[11] Plant 4,353

[45] Dec. 19, 1978

[54] AFRICAN VIOLET PLANT

[75] Inventor: Reinhold Holtkamp, Isselburg, Fed. Rep. of Germany

[73] Assignee: Gessellschaftsvertrag uber die Erfindergemeinschaft "Optimara", Isselburg, Fed. Rep. of Germany

[21] Appl. No.: 880,329

[22] Filed: Feb. 22, 1978

[51] Int. Cl.[2] ..... A01H 5/00

[52] U.S. Cl. ..... Plt./69

[58] Field of Search ..... Plt./69

*Primary Examiner*—Robert E. Bagwill

*Attorney, Agent, or Firm*—Beall & Jeffery

[57] ABSTRACT

An African violet named Wisconsin, which is a mutation of Cornelia. Wisconsin is characterized by its intensive blue-violet flower color and uniform flowering, with the flowers being long lasting and non-dropping. The plant is vigorous and fast growing, producing up to 11 or more flower stems, each carrying four to six flowers, thereby providing a full bouquet when the plant is in full bloom.

1 Drawing Figure

The present invention comprises a new and distinct cultivar of African violet plant, botanically known as *Saintpaulia ionantha*, and hereinafter referred to by the cultivar name Wisconsin. Wisconsin is a mutation of the unpatented and commercial cultivar Cornelia, and Wisconsin was designated during the selection process by the number 26/75. Wisconsin is principally characterized by its intense purple flower color, relatively light green foliage, and by its full bouquet. It also is very uniform in flowering, with flowering appearing on at least 7–9 stems at approximately the same time. The intensive purple flower color and uniform flowering are important distinctions over the parent cultivar Cornelia. The growth characteristics of Wisconsin are similar to Cornelia.

Wisconsin was discovered by me in a controlled environment in Isselburg, Rhineland, Germany, as a mutation of the parent cultivar Cornelia. The new cultivar was discovered growing in a bed of plants of the parent cultivar and had visible distinguishing features. Asexual reproduction of the new cultivar by leaf cuttings and by division of shoots, as performed by me at Isselburg, Rhineland, Germany, has demonstrated that the combination of characteristics as herein disclosed for the new cultivar are firmly fixed and are retained through successive generations of asexual reproduction.

The following observations, measurements and values describe plants grown in Isselburg, Rhineland, Germany, under greenhouse conditions which closely approximate those generally used in commercial practice.

The following traits have been repeatedly observed and are determined to be basic characteristics of Wisconsin, which in combination distinguish this African violet as a new and distinct cultivar:

1. A plant in full bloom has 11 or more flower stems, each of which is straight and approximately 3 mm. in diameter, thereby providing a full bouquet when the plant is in full bloom. The plant is very uniform in flowering, with the first flash of flowers appearing on 7–9 flower stems. This is an important feature from a commercial standpoint.

2. 4–6 flowers on each flower stem, the flowers being nondropping, intensive blue-violet in color, and long lasting.

3. The plant has a compact and vigorous growth habit.

4. The leaves are velvety and relatively tender, and medium to light green in color.

The accompanying photographic drawing shows a typical specimen plant of the new cultivar. The colors appearing in the photograph are as true as possible with color illustrations of this type.

In the following description, color references are made to the Royal Horticultural Society color chart (RHS), 1966 edition, except where general color terms of ordinary significance are obvious.

Botanical classification: *Saintpaulia ionantha*, Ramat. cv. Wisconsin.

Parentage: Mutation of Cornelia.

Propagation: The new cultivar holds its distinguishing characteristics through successive propagations by leaf cuttings and by division of shoots.

Plant: From 9 cm. to 11 cm. tall when grown in pots, and approximately 28 cm. in diameter when fully grown.

*Leaves.*—General Form: oblong. Diameter: 45–50 mm. Texture: soft and velvety. Veins: well pronounced, somewhat reddish. Color (upperside): 137 A, light to medium green. Color (Underside): 149 C. Petiole: reddish, slightly hairy.

Flowers:

*Buds.*—round, diameter 5–7 mm., color 83 B.

*Sepals.*—5 in number, spear-shaped; 4–5 mm. long. Color: reddish, with brown-green secondary hue, 189 A. Calyx: with receptacle and seed-vessel connected. Aspect: funnel-shaped. Peduncle: 22–25 mm. long, diameter 1–2 mm.

Individual flowers:

*Size.*—30–40 mm. in total flower diameter, with the three large petals being approximately 20 mm. long and 16 mm. wide, and the two small petals being approximately 15 mm. long and 13 mm. wide.

*Color.*—Upperside: between 89 B and 89 C. Underside: 88 A. *Borne.*—most flower stems carry up to six flowers.

*Shape.*—Five petals, two small ones and three large ones. Some flowers have more than five petals. They are joined to the receptacle.

*Arrangement.*—Strong straight flower stems with 4–6 flowers on short peduncles.

*Flowering time.*—7–8 weeks after potting the first flowers appear; in 9–10 weeks after potting, the plant is fully in bloom.

Reproductive organs:

*Stamens.*—Two in number.

*Anthers.*—Four anthers, 7 B.

*Arrangement.*—The stamens sit on short stems around the seed-vessel and are fused with the receptacle. They are partially covered by petals.

*Filaments.*—3 mm. long.

*Styles.*—8–9 mm. long, color 89 A

*Pollen color.*—7 C.

Roots: Very well developed root system; the young root tips are white, the older roots are brownish.

Disease resistance: No disease problems noted to date.

General observations: Wisconsin is a very vigorous and fast growing African violet with light green and tender and velvety leaves, which are slightly hairy.

The first flowers uniformly appear as early as 8 weeks after potting, and in 9–10 weeks after potting, the plant is in full bloom. The blue-violet color of the flowers is very intensive, and the flowers are non-dropping and long lasting.

I claim:

1. A new and distinct cultivar of African violet known by the cultivar name Wisconsin and characterized by the combined features of intensive blue-violet flower color, with the flowers being long lasting and non-dropping; uniform flowering; vigorous and fast growing growth habit, producing up to 11 or more flower stems, each carrying four to six flowers, thereby providing a full bouquet when the plant is in full bloom, and soft and velvety leaves, medium to light green in color.

* * * * *

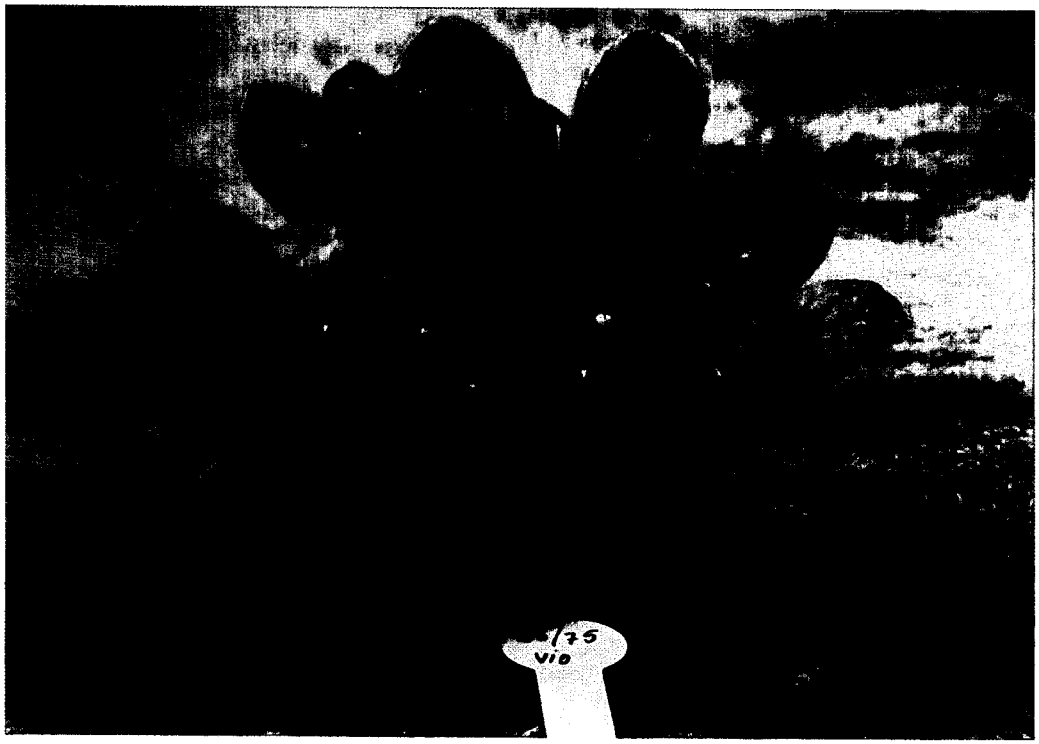
175
VIO